(12) United States Patent
Johansen

(10) Patent No.: US 7,401,530 B2
(45) Date of Patent: Jul. 22, 2008

(54) SONAR BASED MULTIPHASE FLOWMETER

(75) Inventor: Espen S. Johansen, Houston, TX (US)

(73) Assignee: Weatherford/Lamb, Inc., Houston, TX (US)

( * ) Notice: Subject to any disclaimer, the term of this patent is extended or adjusted under 35 U.S.C. 154(b) by 51 days.

(21) Appl. No.: 11/382,761

(22) Filed: May 11, 2006

(65) Prior Publication Data

US 2007/0295101 A1 Dec. 27, 2007

(51) Int. Cl.
*G01F 1/74* (2006.01)
(52) U.S. Cl. .................................. 73/861.04
(58) Field of Classification Search ........................ None
See application file for complete search history.

(56) References Cited

U.S. PATENT DOCUMENTS

| | | | | |
|---|---|---|---|---|
| 6,076,049 | A * | 6/2000 | Lievois et al. | 73/861.04 |
| 6,292,756 | B1 * | 9/2001 | Lievois et al. | 73/861.04 |
| 6,354,147 | B1 * | 3/2002 | Gysling et al. | 73/61.79 |
| 6,601,458 | B1 * | 8/2003 | Gysling et al. | 73/861.04 |
| 6,782,150 | B2 * | 8/2004 | Davis et al. | 73/861.18 |
| 6,813,962 | B2 * | 11/2004 | Gysling et al. | 73/861.26 |
| 6,945,095 | B2 | 9/2005 | Johansen | |
| 7,059,172 | B2 * | 6/2006 | Gysling | 73/32 A |
| 7,134,320 | B2 * | 11/2006 | Gysling et al. | 73/861.18 |
| 7,152,460 | B2 * | 12/2006 | Gysling et al. | 73/861.18 |
| 7,165,464 | B2 * | 1/2007 | Gysling et al. | 73/861.42 |

FOREIGN PATENT DOCUMENTS

| | | |
|---|---|---|
| WO | WO 2005/116637 | 12/2005 |
| WO | WO 2006/112878 | 10/2006 |
| WO | WO 2007/008623 | 1/2007 |
| WO | WO 2007/089412 | 8/2007 |

OTHER PUBLICATIONS

Lievios, et al, Multi-Channel Infrared Optical Phase Fraction Meter, U.S. Appl. No. 11/065,489, filed Feb. 24, 2005.
GB Search Report, Application No. GB0709020.2, dated Sep. 10, 2007.

* cited by examiner

*Primary Examiner*—Harshad Patel
(74) *Attorney, Agent, or Firm*—Patterson & Sheridan, LLP

(57) ABSTRACT

Methods and apparatus determine individual phase fractions for three phases within a fluid mixture. Appropriate flow algorithms can utilize this phase fraction information with a sensed total combined flow rate of the mixture to find individual flow rates for the three phases, such as oil, water and gas. For some embodiments, a multiphase flowmeter includes an array of spatially distributed pressure sensors configured to determine a speed of sound in the mixture and any type of water cut meter, oil cut meter or gas cut meter.

20 Claims, 3 Drawing Sheets

SONAR BASED MULTIPHASE FLOWMETER

BACKGROUND OF THE INVENTION

1. Field of the Invention

Embodiments of the invention generally relate to methods and apparatus for determining individual phase fractions and/or flow rates of multiple phases within a fluid flow.

2. Description of the Related Art

In the petroleum industry, as in many other industries, ability to monitor flow of certain fluids in process pipes in real time offers considerable value. Oil and/or gas well operators periodically measure water/oil/gas phase fraction flow rates within an overall production flow stream containing a mixture of these three phases. This information aids in improving well production, allocating royalties, properly inhibiting corrosion based on the amount of water and generally determining the well's performance.

While some techniques enable measuring flow rates within two phase mixtures, difficulty arises in determining individual volumetric fractions and flow rates in three phase mixtures. Separators can be used to separate out one or more phases from the flow stream but introduce additional equipment, time and costs. Other costly and time consuming procedures entail manual sampling of the mixture to obtain information regarding the individual volumetric fractions. On the other hand, flowmetering devices can be complex and can restrict flow creating significant pressure loss, such as when venturi based measurements are required.

Therefore, there exists a need for improved methods and apparatus that enable determining individual phase fractions and hence flow rates of multiple phases within a fluid flow.

SUMMARY OF THE INVENTION

Embodiments of the invention generally relate to multiphase fluid flow meters. In some embodiments, an apparatus for measuring flow of a fluid mixture in a conduit includes a speed of sound meter disposed along the conduit and configured to determine a speed of sound in the mixture, a phase fraction meter disposed along the conduit and configured to determine a percentage of a first phase within the fluid mixture, and a processor configured with logic to determine phase fractions of second and third phases within the fluid mixture based on evaluation of the speed of sound in combination with the percentage of the first phase.

For some embodiments, an apparatus for measuring flow of a fluid mixture in a conduit includes an acoustic sensing device configured to determine a speed of sound in the fluid mixture with sensors spatially distributed along the conduit to detect acoustic pressure variations traveling at the speed of sound, and a phase fraction device configured to measure a first phase fraction within the fluid mixture and derive from the first phase fraction and the speed of sound second and third phase fractions within the fluid mixture, wherein the phase fractions define separate and distinct phases within the fluid mixture.

According to some embodiments a method of measuring flow of a fluid mixture in a conduit includes measuring a speed of sound in the fluid mixture by sensing along the conduit acoustic pressure variations traveling at the speed of sound, measuring a first phase fraction within the fluid mixture, and determining second and third phase fractions within the fluid mixture utilizing the speed of sound and the first phase fraction, wherein the phase fractions define separate and distinct phases within the fluid mixture.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention relate to multiphase flowmeters capable of determining individual phase fractions for three phases within a fluid mixture. Appropriate flow algorithms can utilize this phase fraction information with a sensed total combined flow rate of the mixture to find individual flow rates for the three phases, such as oil, water and gas. For some embodiments, the multiphase flowmeter includes an array of spatially distributed pressure sensors configured to determine a speed of sound in the mixture and any type of water cut meter, oil cut meter or gas cut meter.

Figure 1:
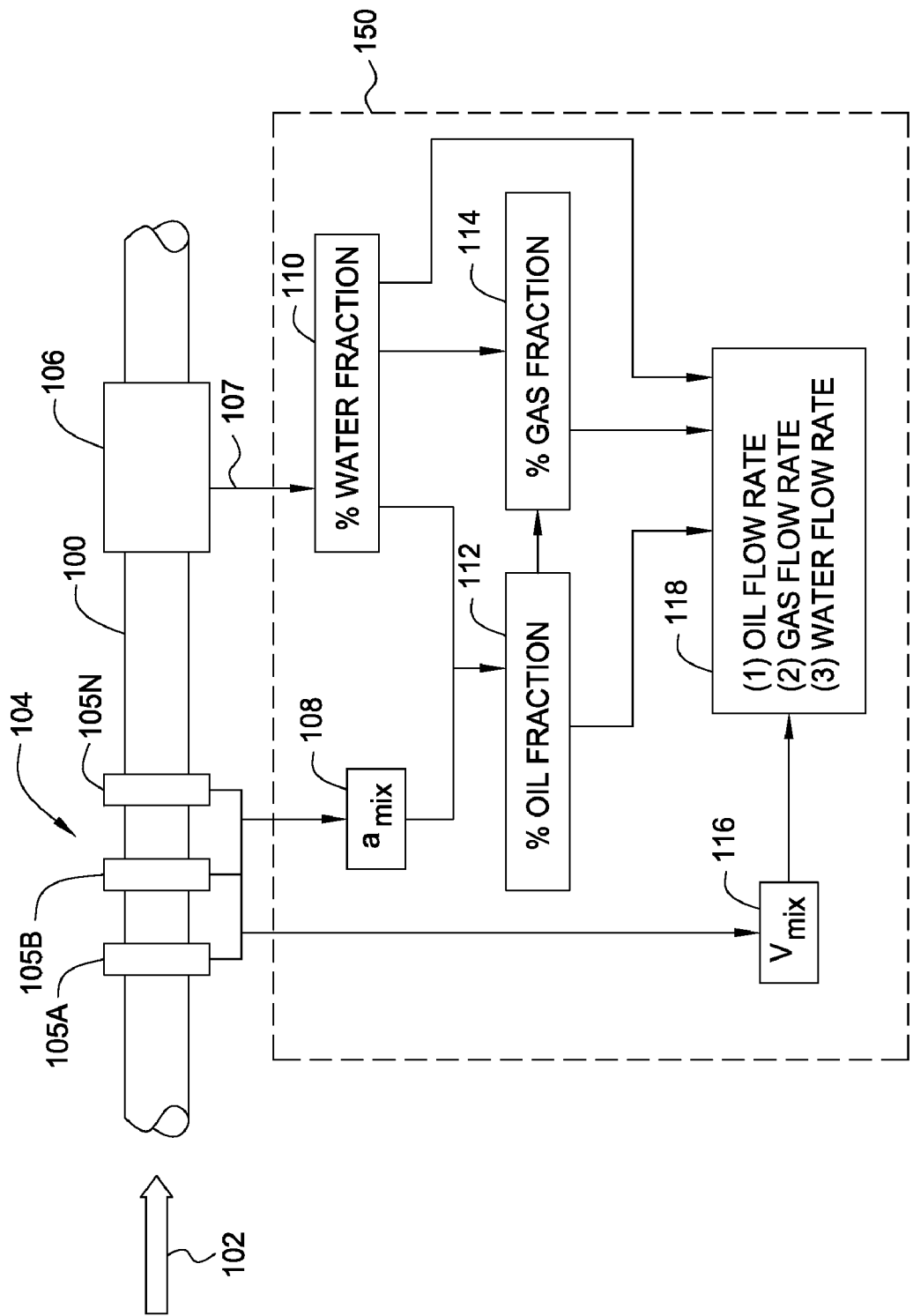
FIG. 1 is a schematic diagram of a multiphase flowmeter system, according to one embodiment of the invention, having a speed of sound and bulk vortical velocity array sensor, a water fraction meter and signal interface circuitry.

FIG. 1 illustrates a multiphase flowmeter system that includes a speed of sound array sensor 104, a water fraction meter 106 and signal interface circuitry 150. As fluid flow 102 indicated by an arrow travels through a conduit 100, the array sensor 104 and the water fraction meter 106 that are both disposed along the conduit sense properties of the fluid flow 102, which can be a mixture of three distinct phases that are oil, gas and water. The signal interface circuitry 150 receives signals from the array sensor 104 and the water fraction meter 106 through transmission lines 107, which may be provided by one or more electrical conductor wires or optical fibers.

The array sensor 104 can include a first pressure sensing element 105A, a second pressure sensing element 105B, and a third pressure sensing element 105N distributed along a length of the conduit 100. In practice, two or more of the sensing elements 105A-N form the array sensor 104 such that the number of the sensing elements 105A-N can be more or less than three as shown. Spacing between the sensing elements 105A-N enables sensing acoustic signals traveling at the speed of sound through the fluid flow 102 within the conduit 100 (referred to as "acoustic sensing") and can also enable sensing short duration local pressure variations traveling with the fluid flow (referred to as "flow velocity sensing"). For some embodiments, coils of optical fiber wrapped around the conduit 100 define each of the sensing elements 105A-N. Other pressure measuring devices such as piezoelectric or polyvinylidene fluoride (PVDF) based detectors can provide pressure time-varying signals with the array sensor 104. The acoustic signals and/or the local pressure variations can originate from naturally occurring phenomenon as the fluid flow 102 travels through the conduit 100.

Regardless of the type of the sensing elements 105A-N utilized, interpretation of these signals from the array sensor 104 enables determination of at least the speed of sound ($a_{mix}$, SOS or $a_{mix}$) of the fluid flow 102 with $a_{mix}$ logic 108. For some embodiments, interpreting the signals from the array sensor 104 with velocity logic 116 permits determination of the velocity ($V_{mix}$) of the fluid flow 102. U.S. Pat. Nos. 6,354,147 and 6,782,150, which are herein incorporated by reference, describe examples of appropriate calculations for determining the $a_{mix}$ and the velocity with similar apparatus that are suitable examples of the array sensor 104 with the sensing elements 105A-N.

The water fraction meter 106 sends appropriate signals to meter phase fraction logic 110 to measure what percentage of the fluid flow 102 is water (i.e., water phase fraction) by techniques such as those provided by microwave water cut meters, spectroscopy based water cut meters, density water cut meters, or capacitive or dielectric water cut meters. As suitable examples of the water fraction meter 106, U.S. Pat. Nos. 6,076,049 and 6,292,756 along with U.S. patent application Ser. No. 11/065,489, which are herein incorporated by reference, describe infrared optical fiber systems for determining the percentage of water within the fluid flow 102. While the following equations assume that the water fraction meter 106 is employed, use of an oil fraction (see, FIG. 2) or a gas fraction meter instead of the water fraction meter 106 requires only minor apparent changes to the following equations and description hereinafter. In other words, combining the measured $a_{mix}$ with a measurement of any one phase fraction enables calculating the corresponding volumetric fractions of the other two phases according to embodiments of the invention. For example, combination of the measured $a_{mix}$ provided by the array sensor 104 with the measured water fraction provided by the water fraction meter 106 can be used as described herein to calculate the volumetric fraction of oil and the volumetric fraction of gas.

Upon determining the $a_{mix}$ in the fluid flow 102 with the array sensor 104 and $a_{mix}$ logic 108 and the water percentage with the water fraction meter 106 and the meter phase fraction logic 110, the oil phase fraction can be calculated based on these measurements using calculation phase fraction logic 112. The calculation phase fraction logic 112 can rely on the following equations and relationships. First, the mixture density is provided by:

$$\rho_m = \sum_{o,w,g} \phi\rho \quad \text{Equation (1)}$$

where $\phi$ is the volumetric fraction and o, w, g denote oil, water and gas, respectively. Further, the mixture isentropic compressibility is given by:

$$\kappa_m = \sum_{o,w,g} \phi\rho^{-1}a^{-2} \quad \text{Equation (2)}$$

In addition, the following defines the oil-to-gas ratio as:

$$OGR = \frac{\phi_o}{\phi_o + \phi_g} = \frac{\phi_o}{1 - \phi_w} \quad \text{Equation (3)}$$

Solving Equations (1) and (2) yields a quadratic equation solvable for the oil phase fraction. Subsequently, the gas phase fraction can be calculated demonstrating ability to solve for both the phase fraction of oil and the phase fraction of gas given $a_{mix}$ and the water fraction. The quadratic equation derived from Equations (1) and (2) is:

$$A\phi_o^2 + B\phi_o + C = 0 \quad \text{Equation (4)}$$

where the terms A, B and C are given by:

$$A = \kappa_o(\rho_o - \rho_g) + \kappa_g(\rho_g - \rho_o) \quad \text{Equation (5)}$$

$$B = \phi_w(\kappa_o(\rho_w - \rho_g) + \kappa_w(\rho_o - \rho_g) + \kappa_g(2\rho_g - \rho_o - \rho_w)) + \kappa_o\rho_g + \kappa_g(\rho_o - 2\rho_g) \quad \text{Equation (6)}$$

$$C = \phi_w^2(\kappa_w(\rho_w - \rho_g) + \kappa_g(\rho_g - \rho_w)) + \phi_w(\kappa_w\rho_g + \kappa_g(\rho_w - 2\rho_g)) + \kappa_g\rho_g - a_{mix}^{-2} \quad \text{Equation (7)}$$

Individual densities and isentropic compressibilities for oil, water and gas are known values. As previously described, values for $\phi_w$ and $a_{mix}$ are measured such that terms A, B and C can be calculated to enable solving for a single unknown that is the oil phase fraction ($\phi_o$) in the Equation (4).

Once the water phase fraction ($\phi_w$) is measured and the oil phase fraction ($\phi_o$) is calculated with the calculation phase fraction logic 112, remaining phase fraction logic 114 calculates the percentage of the fluid flow 102 representing the gas phase fraction ($\phi_g$) according to the following equation:

$$\phi_g = 1 - \phi_o - \phi_w \quad \text{Equation (8)}$$

Flow algorithm logic 118 joins information from the phase fraction logics 110, 112, 114 relating to the volumetric individual phase fractions for each of oil, gas and water with the velocity of the fluid flow from the velocity logic 116 to find individual flow rates for each of the oil, water and gas phases. As an example, U.S. Pat. No. 6,813,962, which is herein incorporated by reference, describes flow modeling techniques applied with velocity or mixture flow rates. The algorithm logic 118 can include assumptions relating to three phase flow such as slippage velocity between liquid and gas phases. The oil flow rate, the gas flow rate and/or the water flow rate may be output from the signal interface circuitry 150 via a display, printout or other user interface.

Figure 2:
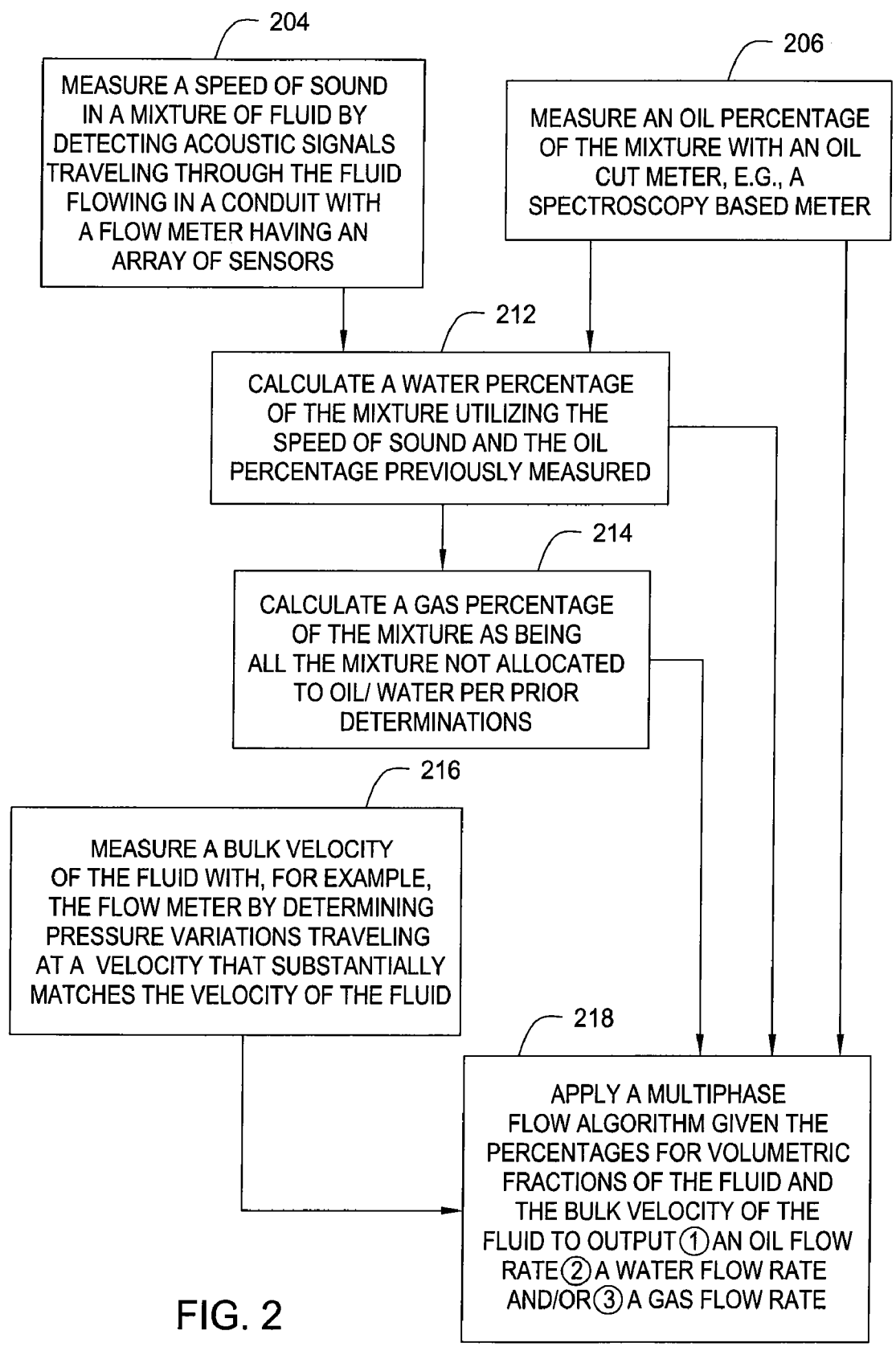
FIG. 2 is a flow diagram, according to one embodiment of the invention, for evaluating with signal interface circuitry multiphase flow rates with a system similar to the system illustrated in FIG. 1 but having an oil fraction meter instead of the water fraction meter.

FIG. 2 shows a flow diagram for evaluating multiphase flow rates with a system similar to the system illustrated in FIG. 1 but having an oil fraction meter (e.g., see, U.S. patent application Ser. No. 11/065,489) instead of the water fraction meter 106. A method of evaluating multiphase flow rates includes, at a SOS step 204, measuring a SOS in a mixture of fluid (e.g., a three phase mixture including a water phase, a gas phase and an oil phase) by detecting acoustic signals traveling through the fluid flowing in a conduit with a flowmeter having an array of distributed sensors. For some embodiments, the conduit forms part of production piping located at a surface of an oil and gas well. At a phase meter step 206, measuring an oil percentage of the mixture occurs with an oil cut meter disposed along the conduit.

Next, information obtained from the phase meter step 206 and the SOS step 204 feeds into an initial phase determination step 212. In the initial phase determination step 212, processing of the SOS and the oil percentage previously measured determines a value for a water percentage of the mixture. A phase remainder calculation step 214 includes determining a gas percentage of the mixture based on any remaining portion of the mixture not allocated to oil and/or water per prior determinations at the phase meter step 204 and the initial phase determination step 212.

When desired to obtain flow rate data for individual phases, a velocity step 216 includes measuring a bulk velocity of the fluid. For some embodiments, this measuring of the bulk velocity includes detecting pressure variations traveling at a velocity that substantially matches a velocity of the fluid. At an output step 218, applying a multiphase flow algorithm given the percentages for volumetric fraction from the phase meter step 204, the initial phase determination step 212, and the phase remainder calculation step 214 and the velocity from the velocity step 216 enables outputting flow rates of oil, water and gas.

Figure 3:
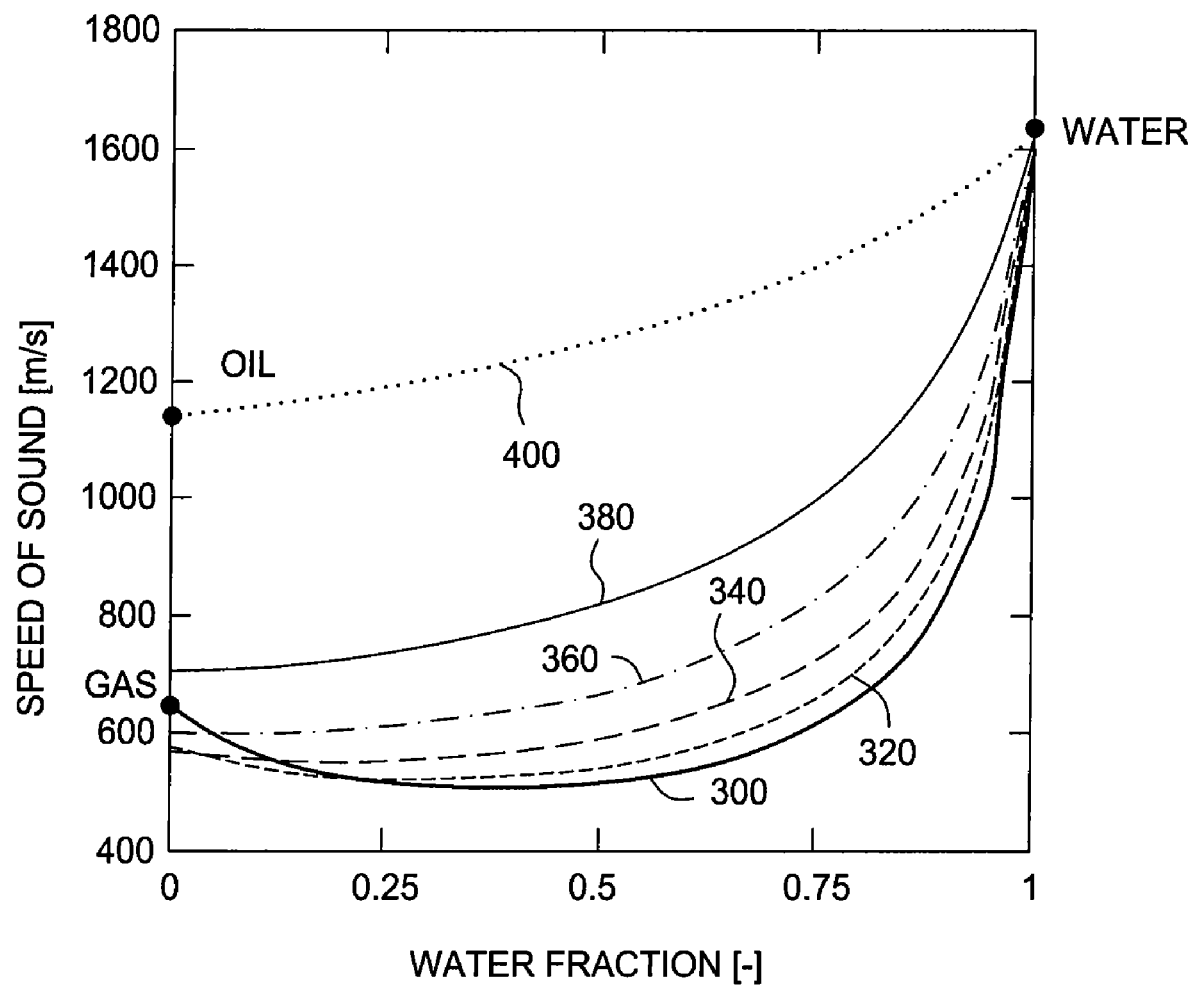
FIG. 3 is a graph of changes in speeds of sound verses water fraction for various oil-to-gas ratios illustrating that a measured speed of sound and a measured water cut functionally corresponds to a particular oil-to-gas ratio enabling determination of such oil-to-gas ratios.

FIG. 3 illustrates a graph of speed of sound verses water fraction for various oil-to-gas ratios. Curves 300, 320, 340, 360, 380 and 400 respectively represent oil-to-gas ratios of 0.0, 0.2, 0.4, 0.6, 0.8 and 1.0. Accordingly, an oil/water curve 400 represent fluid mixtures containing no gas while a gas/water curve 300 represents fluid mixtures containing no oil.

The graph illustrates that a measured speed of sound and a measured water cut corresponds to a particular oil-to-gas ratio enabling calculation of, or even calibration of, oil-to-gas ratios due to changes in speed of sound for a given water cut as a function of oil-to-gas ratio. This graphically illustrates how that the oil-to-gas ratio can be determined by measuring the speed of sound and water cut. Further, a combined oil and gas fraction based on the water cut measurement when applied as in Equation (3) enables determination of the oil phase fraction ($\phi_o$). Calculation of the gas phase fraction ($\phi_g$) hence follows utilizing Equation (8). If desired, the volumetric phase fractions determined can be joined with a total flow rate measurement and a multiphase flow algorithm to find the flow rates of oil, water and gas.

For some embodiments, a separate bulk flowmeter device may be disposed along the conduit 100 to measure a combined flow rate of all phases. The sensor 104 may only therefore need to be configured for detecting the speed of sound of sound and not necessarily the velocity of the fluid flow 102. Measurements relating to the phase fractions within the fluid flow 102 can be obtained in some applications without requiring the velocity of the fluid flow 102 when it is not desired to subsequently obtain flow rate data for the individual phases.

While the foregoing is directed to embodiments of the present invention, other and further embodiments of the invention may be devised without departing from the basic scope thereof, and the scope thereof is determined by the claims that follow.

What is claimed is:

1. An apparatus for measuring flow of a fluid mixture in a conduit, comprising:
    a speed of sound meter disposed along the conduit and configured to determine a speed of sound in the mixture;
    a phase fraction meter disposed along the conduit and configured to determine a percentage of a first phase within the fluid mixture; and
    a processor configured with logic to determine phase fractions of second and third phases within the fluid mixture based on evaluation of the speed of sound in combination with the percentage of the first phase.

2. The apparatus of claim 1, wherein the phases comprise oil, gas and water.

3. The apparatus of claim 1, wherein the first phase is water.

4. The apparatus of claim 1, wherein the first phase is oil.

5. The apparatus of claim 1, wherein the processor further is configured to apply a multiphase flow algorithm to determine flow rates for the first, second and third phases.

6. The apparatus of claim 1, wherein the phase fraction meter comprises an infrared optical based spectroscopy analysis of the fluid mixture.

7. The apparatus of claim 1, wherein the phase fraction meter comprises a microwave based device.

8. The apparatus of claim 1, wherein the phase fraction meter comprises a capacitance based device.

9. The apparatus of claim 1, wherein the meters are optically based and comprise optical fibers.

10. An apparatus for measuring flow of a fluid mixture in a conduit, comprising:
    an acoustic sensing device configured to determine a speed of sound in the fluid mixture with sensors spatially distributed along the conduit to detect acoustic pressure variations traveling at the speed of sound; and
    a phase fraction device configured to measure a first phase fraction within the fluid mixture and derive from the first phase fraction and the speed of sound second and third phase fractions within the fluid mixture, wherein the phase fractions define separate and distinct phases within the fluid mixture.

11. The apparatus of claim 10, wherein the phases comprise oil, gas and water.

12. The apparatus of claim 10, wherein the first phase fraction is a water cut.

13. The apparatus of claim 10, wherein the first phase fraction is an oil cut.

14. The apparatus of claim 10, further comprising a flow velocity sensing device comprising an array of sensors that provide signals indicative of pressure variations in the fluid mixture traveling at approximately the velocity of the fluid mixture.

15. A method of measuring flow of a fluid mixture in a conduit, comprising:
    measuring a speed of sound in the fluid mixture by sensing along the conduit acoustic pressure variations traveling at the speed of sound;
    measuring a first phase fraction within the fluid mixture; and
    determining second and third phase fractions within the fluid mixture utilizing the speed of sound and the first phase fraction, wherein the phase fractions define separate and distinct phases within the fluid mixture.

16. The method of claim 15, wherein the phases comprise oil, gas and water.

17. The method of claim 15, wherein the first phase fraction is a water cut.

18. The method of claim 15, wherein the first phase fraction is an oil cut.

19. The method of claim 15, further comprising providing the conduit at a well to define part of production tubing extending from within the well to a location at a surface of the well.

20. The method of claim 15, further comprising determining a flow rate of the first, second and third phases by applying a multiphase flow model.

* * * * *